(12) United States Patent
Dikovskiy et al.

(10) Patent No.: US 9,446,058 B2
(45) Date of Patent: Sep. 20, 2016

(54) PHARMACEUTICAL COMPOSITION BASED ON A HEPATOPROTECTOR AND A PREBIOTIC, AND PRODUCTION AND APPLICATION THEREOF

(76) Inventors: Aleksander Vladimirovich Dikovskiy, Moscow (RU); Boris Anatolievich Rudoy, Moscow (RU); Oleg Valentinovich Dorozhko, Moscow (RU)

(*) Notice: Subject to any disclaimer, the term of this patent is extended or adjusted under 35 U.S.C. 154(b) by 282 days.

(21) Appl. No.: 12/921,383

(22) PCT Filed: Mar. 4, 2008

(86) PCT No.: PCT/RU2008/000122
§ 371 (c)(1),
(2), (4) Date: Jul. 7, 2011

(87) PCT Pub. No.: WO2009/110816
PCT Pub. Date: Sep. 11, 2009

(65) Prior Publication Data
US 2011/0312910 A1  Dec. 22, 2011

(51) Int. Cl.
*A01N 43/04* (2006.01)
*A61K 31/715* (2006.01)
*A61K 31/66* (2006.01)
*A23L 1/30* (2006.01)
*A23L 1/308* (2006.01)
*A61K 31/685* (2006.01)
*A61K 36/28* (2006.01)
*A61K 45/06* (2006.01)
*A61K 31/702* (2006.01)
*A61K 31/7016* (2006.01)

(52) U.S. Cl.
CPC ............... *A61K 31/66* (2013.01); *A23L 1/30* (2013.01); *A23L 1/308* (2013.01); *A61K 31/685* (2013.01); *A61K 36/28* (2013.01); *A61K 45/06* (2013.01); *A23V 2002/00* (2013.01); *A61K 31/702* (2013.01); *A61K 31/7016* (2013.01)

(58) Field of Classification Search
None
See application file for complete search history.

(56) References Cited

U.S. PATENT DOCUMENTS

2008/0261916 A1* 10/2008 Jaszberenyi et al. ........... 514/58

OTHER PUBLICATIONS

Vanhoof et al. Nutrition Research (1995), vol. 15, pp. 1637-1646.*
Hoshi et al. Journal of Nutrition (1994), pp. 52-60.*
Deutsch et al. Eur. J. Pediatr (1986), vol. 145, pp. 94-98.*
Fasano et al. Digestive Diseases and Sciences (1990), vol. 35, pp. 801-808.*
Donely Seminars in Avian and Exotic Pet Medicine (2004), vol. 13, pp. 8-15.*
Schumann Eur. J. Nutr. (2002), vol. 41, pp. 1/17-1/25.*
Calmus et al. Hepatology (1990), vol. 11, pp. 12-15.*
Lindblad et al. Hepatology (1998), vol. 27, pp. 166-174.*
Sailer et al. Drugs (2001), vol. 61, pp. 2035-2063.*
Flora et al. AJG (1998), vol. 93, pp. 139-143.*
Stratton et al. Best Practice & Research Clinical Gastroenterology (2005), vol. 20, pp. 441-466.*

* cited by examiner

*Primary Examiner* — Patrick Lewis
(74) *Attorney, Agent, or Firm* — Nadya Reingand

(57) ABSTRACT

The invention relates to medicine, hepatology and pharmacology and can be used for producing and using a pharmaceutical composition based on a hepatoprotector and a prebiotic for treating and preventing liver diseases which are caused by lipid-cholesterol exchange and selected from the following group: cholelitiasis mainly with cholesterol stones, alcoholic and non-alcoholic steatohepatitis, biliary cirrhosis, cholesterol imbibition gallbladder and drug-induced and toxic liver damage. The pharmaceutical composition is administered by mouth and contains a hepatoprotector and a prebiotic taken, as an active agent, in therapeutically effective doses. The invention contributes to the liver's functional recovery in a short time and prevents disease recidivation owing to the recovery of cholesterol exchange and intestinal biocenosis as a result of the synergistic interaction of a hepatoprotector and a prebiotic, thereby also preventing hepatoprotector side effects.

15 Claims, No Drawings

PHARMACEUTICAL COMPOSITION BASED ON A HEPATOPROTECTOR AND A PREBIOTIC, AND PRODUCTION AND APPLICATION THEREOF

CROSS-REFERENCE TO RELATED APPLICATION

This application claims the benefit of the priority filing date in PCT/RU2008/000122, as amended and referenced in WIPO Publication WO/2009/110816. The earliest priority date claimed is Mar. 4, 2008.

FEDERALLY SPONSORED RESEARCH

Not Applicable

SEQUENCE LISTING OR PROGRAM

Not Applicable

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

The invention relates to medicine, in particular, to hepatology and pharmacology. It can be used for the production and application of a pharmaceutical composition based on a hepatoprotector and a prebiotic for the treatment and prevention of liver diseases selected from the following group: cholelithiasis, fatty hepatosis and nonalcoholic steatohepatitis, primary biliary cirrhosis, gallbladder cholesterosis, and drug-induced and toxic liver injury.

This is a serious matter because of the higher frequency and severity of liver diseases, the main organ responsible for the detoxification of exogenous toxins. Increased incidences of liver diseases is caused by environmental factors in most world regions.

An additional cause which is directly related to the effect of environmental factors is a population's reduced immunity, resulting in a significant increase of infectious liver lesions, primarily, viral hepatitises.

In the case of viral hepatitis, the source of infection is a sick person, and the infection transmission route is either fecal-oral or parenteral, depending on the type of virus—A, B, C, D, G, or E. A population's susceptibility to type of infection is high.

Regardless of the sight of entry, the virus eventually gets in the liver where it has a direct toxic effect on liver cells, combined with immune-mediated damage to cell membranes. In all forms of viral hepatitis, a serious frequent complication is a disturbance of the normal processes of formation and flow of bile, the so-called "cholestatic syndrome," accompanied by jaundice. It is most often manifested in the case of viral hepatitis A (VHA)—"enteric" viral hepatitis and enteric hepatitis E, wherein the frequency of jaundiced forms is 100%.

In severe forms of acute viral hepatitises (AVH), e.g., chronic hepatisises flowing and exacerbating, the disturbance of the structure and functional activity of biliary ducts is one factor that gives rise to severe complications—biliary cirrhosis.

In addition to viral hepatitises, a large share of liver diseases is due to the effects of food toxicants (alcohol, other toxic substances, and various medicinal agents).

One of the earliest pathological complications in toxic liver injury is steatohepatitis—the result of a disturbance in the normal balance between the input of fats in the body and their metabolism. It should be emphasized that a disturbance in the normal processes of bile formation and biliary passage is one of the widespread consequences of the effect of high doses of a number of drugs (antibiotics, sulfanilamides, chlorpromazine, histamine receptor and estrogen blockers, and cytostatics).

During the last decade, a so-called autoimmune hepatitis, the result of a deep disturbance in the cell immunity system, is being diagnosed more and more often. Its most severe consequence is primary biliary cirrhosis.

Disturbance of the bile production and excretion processes is most vividly pronounced in the form of cholelithiasis, wherein excessive accumulation (congestion) of bile in the gallbladder with subsequent formation of concrements (choleliths or gallstones) is observed.

In all of the above liver diseases, an important ethiologic and pathogenic factor is a disturbance of the normal processes of bile acids (BA) metabolism, one of the most important factors of normal digestion. BAs are formed in the liver from cholesterol (Hofmarm A F. Bile acid secretion, bile flow and biliary lipid secretion in humans. Hepatologi. 1990; 12; 17S; Meier P J. The bile salt secretory polarity of hepatocytes. J. Hepatol. 1989; 9: 124).

Main BAs detected in human bile are cholic acid (CA) (3a, 7a, 12a-trioxy-5b-cholanic acid), chenodeoxycholic acid (CDCA), deoxycholic acid (DCA) (3a, 12a-dioxy-5b-cholanic acid). Stereoisomeres of cholic and deoxycholic acids in the form of allocholic (ACA), ursodeoxycholic (UDCA) and lithocholic (LCA) acids have been detected in bile in considerably smaller quantities.

CA and CDCA, the so-called primary BAs, form in the liver during oxidation of cholesterol, and DCA and LCA form in the intestine from primary BAs due to the effect of enzymes of intestinal flora microorganisms. The normal quantitative ratio of CA, CDCA and DCA in bile is 1:1:0.6.

In the bladder, bile BAs are mainly present in the form of binary compounds—conjugates. In the intestine, mainly in the ileum, BAs are absorbed into the blood, return with the blood to the liver and are again secreted within bile—this is the so-called portal-biliar circulation of BAs; therefore, 85-90% of the entire amount of BAs contained in bile are BAs absorbed in the intestine.

Portal-biliar circulation of BAs facilitates easy absorption of BA conjugates in the intestine because they are water-soluble; in the process, 10-15% of the total amount of BA breaks down in the intestine due to the effect of enzymes of intestine flora microorganisms, and the products of their degradation are excreted with stool.

By emulsifying fats, BAs thus ensure the absorption of insoluble fatty acids and cholesterol in the small intestine, as well as of vitamins B, K, E and calcium salts.

In addition, BAs have a strong choleretic effect, stimulate intestinal motility, and also have a bacteriostatic and anti-inflammatory effect. Taking the above into account, a possible component of the method for the treatment and prevention of a number of pathologic conditions of the liver is the use of bile acid preparations, primarily UDCA.

UDCA is a tertiary bile acid. It was first found in Chinese bear bile in 1902. UDCA has been used in medicine for several centuries. As far back as ancient China, dried bear bile was prescribed for treatment of stomach, intestine and liver diseases. UDCA is formed by the action of bacterial enzymes, from 7-keto-litocholic acid that enters the liver from the small intestine. Herein, all chemical formulae of UDCA and hydrophobic CDCA are identical ($C_{24}H_4O_4$).

Using UDCA for the treatment of, among others, liver diseases, results in a dose-dependent change of the above ratio of bile acids: UDCA becomes the main bile component whereas the content of CDCA and other BAs decrease. Lower accumulation of UDCA in bile is observed in patients with liver diseases, which may be related to reduced absorption, due to reduced formation of endogenous micellae from bile acids in duodenal bile or to reduced secretion of bile acids themselves. As has been stated earlier, UDCA and LCA are detected in human bile in very insignificant amounts (0.1%-5%).

Despite good absorption of UDCA in the intestine, its level in blood plasma remains relatively low due to fast liver clearance. This is due to the effective conjugation of UDCA with glycine, taurine, N-acetoglucosaine, glucuronic acid and sulfate which takes place in the liver.

The effect of UDCA on cholesterol in bile is a complex one as far as it reduces cholesterol absorption in the intestine, and its synthesis in the liver and secretion into bile. However, there is no noticeable decrease of cholesterol level in the blood due to the effect of UDCA. UDCA, and its conjugates that have not been absorbed in the small intestine, are metabolized by indigenous bacteria in the small intestine's distal area and in the colon.

In the intestine, UDCA is broken down and dehydroxylated into lithocholic acid (LCA). LCA, whose content in human blood is very low, is formed in the small intestine due to the action of microflora during the process of utilization of numerous fats. From the small intestine, LCA enters the colon and rectum, where it is partially absorbed, and enters the liver.

In the liver, LCA bonds with sulfate anions and then with glycine and taurine, and in this way is released in bile. Little of its derivatives are absorbed in the intestine and excreted with stool. Such process is an efficient mechanism for the elimination of toxic LCA from the body.

CDCA determines the decrease of the activity of A-oxy-reductase 3-hydroxy-3-methylglutarylcoenzyme—an enzyme that participates in the synthesis of cholesterol. It also facilitates a decrease of cholesterol absorption in the intestine, which results in changing the ratio of bile acids and cholesterol in favor of CDCA bile acids in the common pool.

The above mechanism predetermines the use of CDCA when dissolving gallstones that mainly consist of cholesterol.

Deoxycholic acid (DCA) is a bile acid that is formed in a person's intestine due to the action of intestinal microflora enzymes being absorbed into the blood and secreted by the liver with bile. It is assumed that hydrophobic DCA salt may be the link between disturbed intestinal motility and bile lithogenicity. The main bile acids in humans are CA and CDCA—primary bile acids synthesized in the liver from cholesterol.

Secondary DCA is formed from cholic acid in the small intestine's distal areas and in the colon due to the action of intestinal microflora enzymes, namely, bacterial 7-alpha-dehydroxylase. DCA is partially absorbed from the intestine and involved in the recirculation of bile acids after its conjugation with taurine or glycine in the liver.

An increase in the transit time in the intestine increases DCA formation as a result of bacterial metabolism, while a decrease of the transit time has the opposite effect. As a result, the amount of DCA varies within a wide range—from 10% to 30% of the total pool of bile acids. Recently, it has been proven that patients with cholelithiasis have an increased number of gram-positive anaerobic bacteria, and their 7-alpha-dehydroxylase activity in the colon is higher compared to healthy patients.

In the process, a correlation has been found: slower transit through the intestine, higher DCA share, bile oversaturation with cholesterol, and concrement formation. It is assumed that DCA facilitates bile lithogenicity and concrement formation by slowing the transit time through the intestine, which in turn increases cholesterol absorption and, via the positive feedback mechanism, facilitates the formation of DCA itself. In addition, DCA can increase cholesterol secretion into bile by acting on the canalocular membrane of hepatocytes, where cholesterol is located in sphyngomyelin domains. DCA can also increase cholesterol crystallization in bile, thus destabilizing vesicles with cholesterol. In bladder, bile BAs are mainly present in the form of binary compounds—conjugates. As the result of BA conjugation with amino acid, glycine, glycocholic (GCA) or glycochenodesoxycholic (GCDCA) acid is formed. In BA conjugation with taurine (2-aminoethan-sulfoacid $C_2H_7O_3N_5$), the product of cycteine amino acid degradation, taurocholic (TCA) or taurodesoxycholic (TDCA) acid, is formed. BA conjugation includes stages of formation of CoA-BA esters, and linkage of the BA molecule with glycine or taurine by means of an amide bond, with the participation of a lysosomal enzyme of acyltransferaze. The ratio of glycine and taurine conjugates of BA in bile, 3:1 on average, can vary depending on the composition of food and on the hormonal status of the organism. Thus, a disturbance of bile acids metabolism is an important pathogenic factor of the development of a number of liver diseases.

Known is the method for treatment of the such liver diseases that consists of using UDCA preparations in the form of mono- or complex therapy (RU 2002123352 A of Mar. 27, 2004).

Also known is the method for treatment of liver diseases by using CDCA preparations in complex therapy (Регистр лекарственных средств России. Энциклопедия лекарств [Register of Medicinal Agents of Russia. Encyclopedia of Drugs]. G. L. Vyshkovskiy Editor-in-Chief. M., "RLS"-2006, 2005, pp. 895-896). However, in said treatment methods, a therapeutic effect only develops after a prolonged period (from several months to 6-12 months) of using medications, and often requires essentially taking them for life.

To a large extent, this is due to the fact that the use of BA preparations as monotherapy cannot completely eliminate such important pathogenic factors as intestinal dysbiosis and the complex systemic disturbances of metabolism it causes. As drugs with hepatoprotective properties, one has long been using substances with different structures and mechanisms of action. A lot of professionals challenge the appropriateness of considering them true hepatoprotectors. In particular, the class of so-called essential phospholipids is often added to them. Phospholipids, or phosphoglycerides, are highly specialized lipids. They are important fundamental components of cell membranes and membranes of structural elements of cells, such as the mitochondria, and can be called "essential" (irreplaceable) for growth, development and proper functioning of all somatic cells. In addition to their role in building cell membranes, one can say that phospholipids are important components of lipoproteins, "lung surfactants," and bile. They take part in the operation of the nervous system and in membrane enzyme reactions, and play an important role in metabolism and in oxidation processes. As part of lipoproteins, phospholipids affect the level of cholesterol concentration in blood.

Phospholipids located in trombocites participate in the blood clotting process, which in the end, demonstrates their effect on the protective function of blood and on the hemodynamics of organisms such as mammals and humans. Phospholipids chemical structure, diphility, and the presence of charged groups determine the uniqueness of their physiological properties.

The main function of phospholipids is forming a double lipid layer in cell membranes. The structure and function of cell membranes are extremely important for a person's health. The feeling of general malady, disturbance of functions and various diseases can, in many cases, be explained by damage to or instability of membranes. By introducing phospholipids, one can affect membrane functions related to membrane proteins and correct them, at least to a certain extent, and sometimes completely correct the disturbed function.

Essential phospholipids mainly penetrate liver cells, embed themselves into hepatocyte membranes, normalize liver functions and metabolism of lipids and proteins, facilitate activation and protection of phospholipid-dependent enzyme systems, improve the detoxification function of the liver, restore its cell structure, improve regeneration, and inhibit the formation of connective tissue in it. The preparation reduces the level of energy consumption in the liver, converts neutral fats and cholesterol to easily metabolized forms, and stabilizes bile physical and chemical properties.

Essential phospholipids normalize intestinal digestion not only of fats but also, indirectly, of solid food due to the restoration of the structure of liver cells, which results in the normalization of bile formation and excretion (Gurevich, K. G., Essential Phospholipids in Treatment of Liver Diseases. Качественная клиническая практика [High Quality Medical Practice]. 2002, No. 4, pp. 108-111). Another representative of the group of substances with hepatoprotective properties is milk thistle plant extract as the main active substance in silimarin. It has hepatoprotective, regenerative and detoxification effects. It neutralizes free radicals in the liver and prevents the destruction of cell structures. It specifically stimulates RNC polymerase and activates the synthesis of structural and functional proteins and phospholipids in damaged hepatocytes. It stabilizes cell membranes, prevents the exit of intracellular components (transaminases) and accelerates the regeneration of liver cells. It inhibits the penetration of some hepatotoxic substances (death cup mushroom poison) into the cell.

CLINICAL PHARMACOLOGY: improves the general well-being of patients with liver diseases, reduces subjective complaints (e.g., weakness, feeling of weight in the right hypochondrium, loss of appetite, vomiting and skin itch), and normalizes laboratory parameters, the activity of transaminases, gamma glutamyl and alkaline phosphotase, and bilirubin levels. In prolonged use, it increases the life expectancy of patients with liver cirrhosis.

A number of amino acids or their derivatives are also often considered preparations of the hepatoprotective series. The best known of them is ademethione ((Регистр лекарственных средств России. Энциклопедия лекарств [Register of Medicinal Agents of Russia. Encyclopedia of Drugs]. G. L. Vyshkovskiy Editor-in-Chief, M., "RLS"—2006, 2005, p. 51). This preparation makes up for the deficiency of ademethionine and stimulates its production in the body, primarily in the liver and brain. The S-adenosil-L-metionine (ademethionine) molecule donates the methyl group in reactions involving the methylation of cell membrane phospholipids of proteins, hormones, neuromediators, etc. (transmethylation).

It is the precursor of physiological thyol compounds, e.g., cycteine, taurine, glutathione (provides a redox mechanism of cell detoxification), coenzyme A, etc., in transsulfatation reactions. After decarboxylation, it participates in the process of aminopropylation, as the precursor of polyamines, e.g., putrescine (stimulator of cell regeneration and proliferation of hepatocytes), spermidine and spermine, that are part of ribosomes structure.

It has an anticholestatic effect and is effective in the intralobial version of cholestasis (disturbance of bile synthesis and flow). The anticholestatic effect is due to increased motility and a polarization of hepatocyte membranes due to the stimulation of phosphatidylcholine synthesis in them. This improves the function of hepatocytes which are involved in the transport systems of bile acids (BAs) associated with membranes, and facilitates BA passage into the bile excretion system.

It stimulates BA detoxification, i.e., increases the content of conjugated and sulfated BAs in hepatocytes. Conjugation with taurine increases the solubility of Bas and their elimination from hepatocites. Sulphatation makes elimination by kidneys possible. It facilitates hepatocyte passage through the membrane and excretion with bile. In addition, sulphated BAs protect liver cell membranes from the toxic action of non-sulphated BAs (present in high concentrations in hepatocites in intrahepatic cholestasis).

In patients with diffuse liver diseases (cirrhosis, hepatitis) with intrahepatic cholestasis syndrome, it reduces the intensity of skin itch and changes of biochemical indices, including the level of conjugated bilirubin, ALP activity, aminotransferases, etc.

Therapy was accompanied by the disappearance of asthenic syndrome in 54% of patients and a decrease of its intensity in 46% of patients. The antiasthenic, anticholestatic and hepatoprotective effects continued for 3 months after the treatment was stopped. Their efficiency in the case of hepatopathies caused by hepatotoxic medicinal agents (paracetomol, etc.) has been demonstrated. As a result of treating patients with opiate drug addiction accompanied by liver injury, the following were observed: regression of clinical manifestations of abstinence, improved functional condition of the liver and microsomal oxidation processes, and an anti-depressant effect.

THE USE: intrahepatic cholestasis; liver injuries—toxic, including alcoholic, virus and drug-induced (antibiotics; anticancer, antituberculous and antivirus preparations; tricyclic antidepressants; and oral contraceptives); cirrhotic and pre-cirrhotic conditions; encephalopathy, including encephalopathy associated with hepatic failure (alcoholic, etc.); depressive and abstinence syndromes. In addition to directly affecting the liver tissue, ademethionine has a number of additional pharmacological effects, such as antidepressant action (develops during the first week and stabilizes during the second week of treatment). This preparation is also used empirically in osteoarthrytises; this is accompanied by reduced pain syndrome, by stimulation of proteoglycans synthesis, and by partial regeneration of cartilaginous tissue.

However, the use of essential phospholipids in liver disease therapy, as well as for other hepatoprotectors, usually does not result in full recovery. When the preparations are cancelled, there are often recurrences or exacerbation of liver diseases, including persistent disturbance of intestine biostenosis, which is stubborn in a number of gastrointestinal tract organ and liver diseases.

In recent years, the concept of unity of all processes taking place in gastrointestinal tract pathology has been getting increasing recognition in gastroenterology. Within the framework of this concept, one of the most important components of this normal state is the normalization of colon microflora. The microflora of the gastrointestinal tract (GIT) and the liver closely interact in the processes of organism detoxification. Microbiota in biofilm is the first one to get in contact with all substances entering the body as food, water or atmospheric air and is responsible for all subsequent metabolic reactions. Microbiota converts chemical substances to non-toxic end products or to intermediate compounds that are easily broken down in the liver and then eliminated from the body.

The body has two main detoxifying organs, the liver, which protects the body by means of oxidation reactions, and the digestive tract microflora, which detoxifies using hydrolytic reduction processes. A disturbance in the interaction of these systems mutually results in functional and structural changes in them and in the body as a whole. This is why the enterohepatic circulation of various organic and inorganic substances can be considered among the cardinal homeostatic mechanisms of the body. A decrease in the detoxification function of GIT microflora in dysbiosis, caused by various pathogens (drugs, food, stress, etc.), increases the load on the enzyme systems of the liver, and under certain conditions, facilitates the appearance of metabolic and structural changes in the GIT microflora.

In the case of an imbalance in the digestive tract microecology, an increased proportion of potentially pathogenic gram-negative bacteria results in a substantial accumulation of endotoxins in the lumen of the intestine. As endotoxins penetrate the local blood circulation system through intestinal mucosa and enter the liver through the portal vein, they damage hepatocites or potentiate adverse effects in other toxicants. Ninety percent of all endotoxins are freed facultatively by gram-negative bacteria. Endotoxins damage cell membranes, disturb ion transport, cause fragmentation of nucleic acids, induce the formation of free radical oxidation products, initiate apoptosis, etc. (Gracheva, N. M., et al. Chilak-Forte in Complex Treatment of Patients With Acute Intestinal Infections and Chronic Diseases of Gastrointestinal Tract With Effects of Dysbacteriosi. Consilium medicum. 2004, No. 1, pp. 31-34). Therefore, one of the possible ways to correct disturbances in the microbiota and liver interaction complex is to fight intestinal dysbiosis.

Known is the method for the normalization of intestinal microflora by oral (per os) administration of probiotics—live bacteria, species and genera normally colonizing the colon of humans and other mammals (V. F. Dyomin et al. The Experience of Using Biophitocorrection in Children With Disbiosis. Вопросы современной педиатрии [Journal of Modern Pediatrics], 2003, No. 3, vol. 2, pp. 33-36). However, the use of probiotics in the form of monotherapy does not produce sustainable effects because of the "foreignness" of bacteria strains and their fairly rapid elimination (3-5 days) after the administration of the medicinal agent (MP) ceases.

Other preparations are used for the correction of disturbances of intestinal microbiota—prebiotics do not have this shortcoming. Probiotics, among other things, include a lot of oligosaccharides that are not utilized by the human body because the intestine does not have its own enzymes that break up such sugars. Among non-digestible oligosaccharides are, in particular, fructooligosaccharides (FOS), maltooligosaccharides, galactooligosaccharides, inulin, lactulose and a few other oligosaccharides that can be used as prebiotics (Sheveleva, S. A., Probiotics, Prebiotics and Probiotic Products. State of the Art. Вопросы питания [Journal of Nutrition], 1999, No. 2, pp. 33-39; Shoaf K et al. Prebiotic galactooligosaccharides reduce the adherence of Enteropathogenic *Escherichia coli* to tissue culture cells. Infect Immim., 2006, Sep. 18. Abstr.).

As far as their chemical structure is concerned, FOS are oligofructosaccharides, wherein $\beta$-, D-fructofuranose residues are connected to each other by $\beta$-2, 1-glycoside bonds, and on one end of the chain they have $\alpha$-glucose residue connected to fructose by $\alpha$-1, 2 bond. They can be considered derivatives of saccharose, with 1 to 3 fructofuranose residues connected to its fructose part by $\beta$-2, 1 bonds. The main components of FOS are 1-chestose ($GF_2$), nistoze ($GF_3$) and IF-fructofuranosylnistose ($GF_4$). FOS have a pronounced prebiotic effect, i.e., they are not digested in the upper GIT, they suppress the growth of putrid microflora, they facilitate the normalization of blood pressure and the level of lipids in blood, they improve the adsorption of calcium and magnesium, they increase immunity, they have a beneficial effect on constipation and purulent processes, and they prevent colon cancer.

Like all prebiotics, FOS are not hydralized by GIT ferments, they are not absorbed in the small intestine, and, upon entering the colon unchanged, they are a selective substrate for the growth of normal microflora.

Lactulose is a disaccharide consisting of galactose and fructose (4-0-D-galactopyranosyl-D-fructose). In vivo, lactulose in small quantities can form when milk is heated to temperatures above 100° C. Lactulose is very soluble in water and about 1.5-2 times sweeter than lactose. The prebiotic effect of lactulose increases the volume of colon contents, decreases pH levels, decreases the ammonia content in the colon and increases the content of short-chain fatty acids, particularly propionic acid (ZDUNCZYK Z et al. Physiological effects of lactulose and inulin in the caecum of rats. Arch Anim Nutr., 2004. Vol. 58(1), pp. 89-98).

Also known is the lactulose effect on intestinal microflora, i.e., increasing the number of bifidobacteria with the increased activity of microbial $\beta$-galatosidases (BOUCHNIC Y et al. Prospective, randomized? Parallel-group trial to evaluate the effects of lactulose and polyethylene glycol-4000 on colonic flora in chronic idiopathic constipation. Aliment. Pharmacol. Ther., 2004, Vol. 19(8), pp. 889-899).

Until now, lactulose has been a prebiotic, and, at the same time, has been used in therapy, mainly or even exclusively, as a mild and effective laxative. The laxative effect of lactulose is due to its prebiotic effect and is caused by an increased volume of colon contents (by about 30%) because of the increase in the bacterial population.

For instance, known is the method for the normalization of disorders of the intestinal microflora that includes the use of prebiotics, particularly indigestible oligosaccharide (lactulose, FOS, etc.) (JP 2003-155242 of May 27, 2003). In literature, there is very little information about attempts to use prebiotics for the treatment of liver diseases.

According to published data (Nikitin, I. G. et al., Duphalac (Lactulose) in Treatment of Intestinal Dysbiosis in Nonalcoholic Steatohepatitis. Клинические перспективы гастроэнтерологии, гепатологии, колопроктологии [Clinical Prospects of Gastroenterology, Hepatology, and Coloproctology], 2002, No. 1, pp. 24-29; Savelev, V. S., Lipid Distress Syndrome in Surgery. Вестник Российской военно-медицинской академии [Bulletin of the Russian Military Medical Academy], 1999, No. 1, pp. 36-39), the use of prebiotics as mono-preparations by itself has little effect when attempting to treat liver diseases. This is because the damage to cells, and accordingly damage to the functions of liver tissue, is not completely eliminated.

The therapeutic effect of only using prebiotics occurs after a fairly long period, and in such case, a complete restoration of the disturbed lipid metabolism, and particularly of cholesterol metabolism, is not achieved. Moreover, in the referenced studies, lactulose was used in large doses (on the order of 30 ml of concentrated syrup per person) as laxatives and not as prebiotics. Usually, lactulose is used in hepatology in such large doses to alleviate symptoms of liver encephalopathy, i.e. in palliative symptomatic alleviation for patients with already practically incurable conditions (advanced stage cirrhoses). In these situations, the normalization of intestinal microflora cannot provide any long-term effect. Therefore, in the various disease therapy schemes, schemes involving the complex application of various groups of medicinal agents, for instance, immunomodulators and antibiotics, choleretics, etc. are more widely used.

In this respect, particularly known is the method for the treatment of chronic non-calculous cholecystitis with manifestations of dysbiosis due to the use of a combination of a hepatoprotector (glutargin) and an eubiotic (bifiform) (UA 70018 of Sep. 15, 2004). However, the therapeutic result of this combination is short-term due to the noted earlier limitations related to the use of probiotics. Also known is the method for the treatment of liver diseases with cholestatic syndrome by using a combination of a phytogenic hepatoprotector (extract from *Silibum marianum*) and a probiotic strain of *Lactobacillus bulgarinii*, along with a few other substances (BG 108250U of Apr. 30, 2005). However, in this case too, the positive therapeutic effect is relatively short-term.

Known is the method for the correction of Savelev's lipid distress syndrome using complex therapy including a phytogenic hepatorpotector—gepabene, and metabolite probiotic chilac-forte (Petukhov, V. A., Liver Function Abnormality And Dysbiosis in Lipid Distress Syndrome. РМЖ [RMZh], 2002, No. 10, Vol. 4, pp. 158-160). However, in this analogue, neither the scheme of treatment using these means nor their doses or ratios are specified. Moreover, the interaction of the medicinal agents used is not shown.

Also known for the treatment of liver diseases is a combined preparation comprising alkaline sphingomyelinase as the main acting agent, and various substances, including substances from the class of probiotics (*Lactobacillus acidophilus, Lactobacillus brevis, Lactobacillus buchneri, Lactobacillus casei, Lactobacillus catenaforme*) and UDCA, as additional means (EA 5166 of Dec. 30, 2004).

In the above analogue, the leading role is played by sphingomyelinase (a lysosomal enzyme), which is used for the prevention and/or treatment of various diseases from the following group: small intestine disorder, malignant tumors, immune system disturbance, inflammations and desquamation of the mucous membrane of the small intestine, conditions associated with disturbances in the synthesis of cholesterol, disturbances of absorption ability of the small intestine, and allergy diseases of the small intestine. Herein, said pharmaceutical composition includes, as additives, probiotics (*Lactobacillus acidophilus, Lactobacillus brevis, Lactobacillus casei*, etc.), ursodeoxycholic acid (i.e., a bile acids derivative) and a prebiotic (i.e., lactulose).

But the patent description does not disclose the role of these additives in the treatment of liver diseases, and there is no scientific justification for including them in this composition.

The use of the pharmaceutical composition for the treatment of said diseases is not without a main shortcoming, i.e., a short-term effect caused by an exogenous probiotic strain. Herein, prebiotic components present in the composition are to a large degree utilized by said introduced exogenous strain.

In addition, the inclusion in the composition of a large number of components with a different type of action does not make it possible to evaluate their role and therapeutic effect, nor does it preclude mutual antagonism of such effects, which increases the probability of individual variations in reaction to the administration of such large number of preparations.

The closest analogue of the claimed invention is an agent or component that improves the liver function, acts as the methyl group donor, includes a not easily assimilated oligosaccharide that comprises galactose, and is used as a functional nutrition product (JP 2003-155242 of May 27, 2003). Herein, the methyl group donor is selected from a group of amino acids that includes S-adenosylmethionine, and the galactose-containing oligosaccharide is selected from a group that includes, among others, lactulose or galactooligosaccharide. However, in said patent, the authors do not consider the prebiotic effects of the composition, and in the proposed agent, the authors reduced the role of the oligosaccharide component (and only supposedly at that) in the elimination of ammonia-induced hepatoencephalopatic intoxication. As such, the authors of the closest analogue do not link the lipid metabolism normalizing effect of the compounds, i.e., the donors of the methyl groups to the normalization of the condition of intestinal microbiocenosis, and the examples provided make no mention of this condition.

The lack of understanding of the inseparable interrelation of the condition of intestinal microbiocenosis and lipid metabolism reactions, and the role of normal microflora representatives in breaking the vicious circle of enteropathogenic recirculation of bile acids, do not make it possible to correctly select the component content of the compositions based on the degree of disturbance of these important components of the metabolic process. Moreover, they also do not make it possible to control to the necessary degree the adequacy and effectiveness of the therapy of liver diseases that is performed. By reducing the role of the first component of the composition just to the function of the methyl group donor, the authors unreasonably ignore other mechanisms that disturb lipid metabolism, particularly of cholesterol metabolism, that plays the most important role in the development of many liver diseases.

The distinction of the claimed method from the closest analogue is as follows:

the liver diseases that are different from the closest analogue and for treatment of which a real pharmaceutical composition has been developed are clearly defined;

a pharmaceutical composition has been developed that comprises a hepatoprotector and a prebiotic selected strictly from a limited number of representatives of these groups of medicinal agents; the advisability of simultaneous introduction of a hepatoprotector and a prebiotic in one pharmaceutical composition because of their synergistic effect on each other is demonstrated;

the ratio of the hepatoprotector and the prebiotic in the claimed pharmaceutical composition has been identified.

The objective of the invention is to achieve substantial positive effects in the form of accelerating the normalization of health and reducing the intensity of disease symptoms in the case of complex treatment of individual liver diseases. Said objective is achieved by using, in the therapy of liver diseases, a combined (complex) medicinal agent containing a mixture of a hepatoprotector and a prebiotic substance, particularly oligosaccharides that are not digestible in the intestine. The technical result that the invention aims to achieve is to restore liver functions as soon as possible and to prevent the recurrence of disease by restoring cholesterol metabolism and intestinal biocenosis caused by the synergistic interaction of the hepatoprotector and the prebiotic, which also inhibits hepatoprotector side effects. As the hepatorpotector, the invention uses bile acids/bile acid salts selected from the following group: GCA, GCDCA, TCA, TDCA, UDCA, CDCA, and essential phospholipids.

The presence of a hepatoprotector and a prebiotic in the claimed pharmaceutical composition ensures a pronounced and sustainable therapeutic effect due to the synergistic effect of the hepatoprotector and the prebiotic. The synergistic effect of a hepatoprotector, for instance, UDCA, and a prebiotic is due to the fact that UDCA normalizes intestinal digestion not just of fats, but also of solid food, due to the increased synthesis of bile acids and the UDCA itself in the liver. This in turn facilitates the normalization of intestinal microflora, while the prebiotic by itself facilitates the normalization of microflora by stimulating the growth of resident strains. Stimulating the growth of resident strains results in the manifestation of immunity-stimulating effects and other effects of normal flora. This results in an improvement of digestive properties and consequently in an improved detoxification of exogenous toxins by microflora, which also reduces the metabolic load on the liver and facilitates the normalization of the metabolism of fatty acids and cholesterol. This has a stabilizing effect on all body cells, including hepatocites. Thus, combining bile acids or bile acid salts in one pharmaceutical composition with oligosaccharides that are not digestible in the small intestine and that are chosen from a group of lactulose or FOS, maltooligosaccharides, galactooligosaccharides, or inulin, makes it possible to restore the function of hepatocites, and the liver as a whole, due to the normalization of intestinal biocenosis, which in turn ensures a long-term stabilization of the achieved therapeutic result.

It is well known that in liver diseases and cholelithiasis with mainly cholesterol stones, one observes a higher content of toxic products in a patient's blood that enter the blood from the colon, especially ammonia, a nitro compound that forms in the process of bacterial decomposition of protein by proteolytic microflora in the colon, which increases the toxic load on the liver. Thus, the restoration of microflora in the intestine indirectly facilitates the decrease of the toxic load on the liver and the increase of UDCA in the liver, which in turn facilitates the restoration of bile composition. In particular, an increase of bile acids due to a decreased synthesis of cholesterol by the liver, in turns prevents a recurrence of the disease, particularly of cholelithiasis with mainly cholesterol stones. Taking the above into account, the active components in the presented pharmaceutical composition mutually amplify the therapeutic properties each of them has.

The claimed pharmaceutical composition can include various substances with hepatoprotective properties as the active agent, particularly a hepatoprotector (selected from the following groups: amino acids or their derivatives, active hepatoprotective substances from milk thistle plant extracts (silimarin, silibinin)), essential phospholipids, or bile acids/bile acid salts (selected from the following group: CA, CDCA, DCA, UDCA, HDCA, TUDCA, TCA, and GCA in the unit dose from 50 mg to 500 mg), and a prebiotic (selected from the group of oligosaccharides non-digestible in a human intestine, such as lactulose, or fructooligosaccharide (FOS), or maltooligosaccharides, or galactooligosaccharides, or inulin, taken each in the effective therapeutic prebiotic dose, galactooligosaccharides, maltooligosaccharides or xylooligosaccharides, with the hepatoprotector to prebiotic ratio from 1:2 to 1:250).

The claimed pharmaceutical composition can be made in the form of tablets (coated or uncoated), granules, globules, powder, capsules, suspensions, emulsions, or gels.

In doing so, the claimed pharmaceutical composition can additionally comprise additives that are generally accepted in the pharmaceutical industry, such as microcrystalline cellulose or lactose, corn starch, potato starch, hydroxypropylmethylcellulose, carboxymethylcellulose, oxypropylmethylcellulose, oxypropylcellulose, their pharmaceutically acceptable salts, ludipress, calcium stearate, magnesium stearate, polysorbate, polyvinyl pyrrolidone, polyethylene glycol, talcum, titanium dioxide, or silicon dioxide.

The claimed composition is prepared by mixing the components comprising it, both of which are active, —the hepatoprotector (selected from the following group: essential phospholipids or bile acids/bile acid salts, and the prebiotic) and the additives (selected from the following group: microcrystalline cellulose, lactose, corn starch, potato starch, hydroxypropylmethylcellulose, carboxymethylcellulose, oxypropylmethylcellulose, oxypropylcellulose, their pharmaceutically acceptable salts, ludipress, calcium stearate, magnesium stearate, polysorbate, polyvinyl pyrrolidone, polyethylene glycol, talcum, titanium dioxide, or silicon dioxide).

The claimed pharmaceutical composition is administered orally, and is washed down with a large amount of water for a period of 1.5 to 3 months.

The claimed pharmaceutical composition can be used for the treatment of patients with liver diseases (selected from the following group: cholelithiasis with mainly cholesterol stones, alcoholic and non-alcoholic steatohepatitis, primary biliary cirrhosis, gall bladder cholesterosis, and drug-induced and toxic liver injury), and makes it possible to achieve long-term remission of the disease in a relatively short period of time (6 to 12 weeks). Herein, the therapeutic effectiveness is 89% to 95%.

The claimed pharmaceutical composition does not have contraindications and can be used for the treatment of patients with the liver diseases listed above, including against the background of severe concomitant diseases (except advanced stages of liver cirrhosis, malignant tumors of gastrointestinal tract or other organs), regardless of the patient's age.

The claimed composition does not have significant side effects because the active components in the pharmaceutical composition are used in small and medium unit therapeutic doses and during a fairly short period of time. The proposed versions of the composition are characterized by low cost and are therefore affordable for all categories of patients.

Patient treatment is performed outpatient and does not require patients to keep bed rest or a semi-strict bed rest regimen, which makes it possible for patients to lead normal lives.

The proposed pharmaceutical composition can be successfully used not just for treatment but also to prevent exacerbations of liver diseases (selected from the following group: cholelithiasis with mainly cholesterol stones, alcoholic and non-alcoholic steatohepatitis, primary biliary cirrhosis, gall bladder cholesterosis, and drug-induced and toxic liver injury) due to a restoration of the structure and function of both hepatocytes and the function of the liver as a whole caused by a normalization of intestinal microflora. The effect of the proposed pharmaceutical composition on the body in a certain dosage stimulates a gradual and increased enhancement of the therapeutic effect and connects new levels of homeostasis regulation (e.g., the sub-cell, inter-cell, tissue, organ, system and body levels) due to the restoration of lipid metabolism, particularly cholesterol metabolism, because of the normalization of intestinal microbiocenosis.

During treatment, which is performed outpatient, the patient should maintain a regimen of at least three meals a day during the entire treatment period; alcohol, fatty and spicy food and other medicinal agents are not recommended; fasting and hard physical work are prohibited.

The final diagnosis is determined based on additional types of examinations (USE of the liver or radiology of bile passages) and laboratory blood tests (biochemistry: cholesterol and its fractions, biliburin and its fractions, alkaline phosphotase, GPT, AST, ESR, etc.). We examined 60 patients. In all patients, clinical symptoms of liver injury of various degrees of manifestation had been found: ochrodermia of the skin and sclera, skin itch, a sense of discomfort or feeling of weight in the right hypochondrium, dyspetic effects, e.g., nausea, anorexia, vomiting, weakness, atony, change in the color of urine (darker) and stool (loosening or diarrhea).

All patients had been treated earlier, either outpatient or inpatient, using various medicinal agents. Most patients (37 out of 60) had concomitant diseases: chronic gastroduodenitis and cardiovascular system (CVS) diseases (e.g., hypertensive disease (HD), ischemic heart disease (IHD)), lung diseases (e.g., pneumosclerosis, bronchial asthma (BrA), etc.). Moreover, in 85% of patients, concomitant disturbances of the state of colon biocenosis were identified. For all patients in the experimental groups (50), treatment using the claimed pharmaceutical composition was performed in the dosing regimen that had been developed, i.e., 3 times a day at meal time for 1.5-3.0 months. By the end of the second week, the detoxification and synthetic function of the liver had been restored in all 50 patients regardless of the character of liver injury, while intestinal biocenosis was restored.

All patients noted a relief of discomfort in the right hypochondrium and an improvement of general health as early as the fifth day. By the start of the second week, there was a disappearance of dyspetic disorders, a restoration of appetite, a normalization of the urine and stool, a disappearance of skin itch and a restoration of the original skin color while a significant improvement in the general condition and mood was observed subjectively in all patients. Simultaneously, a relief or disappearance of concomitant pathology symptoms was noticed. In biochemical blood tests by the end of the third week, a normalization of all biochemical indexes, including those characteristic of liver operation and lipid metabolism was noted.

EXAMPLES OF EMBODIMENT OF THE METHOD

1. Patient I., male, 46 years old.

On admission, there were complaints of aching pain in the right hypochondrium, radiating to the right shoulder, appearing 3-4 hours after consuming fatty food, or after a lavish meal, or after physical exertion. There were also complaints of general weakness, anorexia, nausea, periodic vomiting, a feeling of bitterness in the mouth, stool loosening, sometimes diarrhea, skin itch, change in the color of the urine (darker) and stool (lighter). From the anamnesis: cholelithiasis for 10 years; has not been operated; has been treated outpatient, without much effect; worsening after physical exertion. Objectively: supernutrition, weight 75 kg, height 167 cm, skin pale, with traces of scratching on the back and abdomen; Icteric sclera. Abdomen was soft and painful at the Kehr point; Kehr's, Mussy's and Murphy's symptoms were positive; Liver was at the edge of the coastal arch; Vesicular breathing in the lungs; Breathing rate was 18 a minute. Cardiac border was within the age norm; Sounds moderately deadened, rhythm regular, heart rate 78 a minute, BP 140/85 mm Hg. Pasternatsky's syndrome was negative on both sides. Provisional diagnosis: Chronic cholecystitis in the exacerbation phase.

Examination:

Complete blood count: Hb 123 g/l; erythrocytes (ER) $4.11 \times 10^{12}$/l; color index (CI) 0.89; leukocytes $4.0 \times 10^9$/l; stab (S) leukocytes (L) 2%; segmental leukocytes (S) 46%; eosinophils (E) 5%; lymphocytes (L) 45%; monocytes (M) 2%; ESR 40 mm/h. Complete urinalysis: relative density 1016; no protein or glucose detected; leukocytes 0-1-3 in field of view; erythrocytes 0 in field of view; urine amilase 16.2 mgs/l.

Coprogram: muscle fibers without striation—a little; fatty acids—moderate amount; undigested phytogenic fiber—a lot; starch; isolated cells.

Feces on dysbacteriosis: Reduction of the number of bifidobacteria and lactobacilli, respectively: $10^5$/g and $10^6$/g, due to increase of *Candida* fungi. Blood biochemistry: bilirubin and its fractions: total bilirubin (TB)—22.8 µmol/l (N—3.4-20.5 µmol/l); conjugated bilirubin (CB)—3.8 µmol/l (N—0.85-3.4 µmol/l), non-conjugated bilirubin (NCB)—11.7 µmol/l (N—2.56-10.3 µmol/l);

thymol test (TT)—12.1 units (N—4 units), ACT—79 units (N—60 units) GPT—72 units (N—50 units), thymol test (TT)—1.7 units (N—4 units), alkaline phosphatase (ALP)—362 units (N—up to 295 units), CCC 15.3; sugar 3.5 mmol/l (N—4.4-6.6 mmol/l);

cholesterol and its fractions: total cholesterol (TC)—5.5 mmol/l (N—3.65-5.2 mmol/l), high-density lipids cholesterol (HDLG)—0.8 mmol/l (N—0.9-1.9 mmol/l), low-density lipids cholesterol (LDLC)—3.2 mmol/l (N—1.91-2.6 mmol/l), cholesterol atherogenic ratio (CAR) 3.5 c.u. (N—up to 3 c.u.), CCC 15.3 (N—up to 12);

protein fractions: total protein 67 g/l (N 65-85 g/l); albumins 34 g/l (N—36-50 g/l);

antinuclear antibodies: AMA titer 1:10;

coagulogram: PTR 24 s—79%; thrombine clotting time 35 s; free heparin 12 s; fibrinogen 2.2 g/l; fibrinolytic activity>240 min.

Coprogram: dysbacteriosis due to reduction of lactobacilli and bifidobacteria: lactobacilli ($10^5$) (N>=$10^7$/g), bifidobacteria ($10^7$) (N>=$10^9$).

Radiography of the liver and bile passages—indirect signs of calculus cholecystitis, stones do not contrast. Recommended: USE of the liver and gallbladder.

USE of the liver—chronic cholesistisis, cholesterol stones: 0.9, 1.2, 1.5, 1.3 mm, edges even.

EKG—sinus rhythm, signs of moderate left ventricular hypertrophy. BP 150/85 mm Hg; heart rate 74 a minute.

Final diagnosis: Lipid metabolism disorder, hypercholesterinemia. Chronic calculous cholecystitis (cholesterol stones) in the exacerbation phase.

Treatment: the use of the claimed composition, wherein the active agents are a hepatoprotector—UDCA and lactulose in the ratio of 1:2 (unit dose of UDCA is 325 mg), orally 3 times a day at meal time for 1.5 months while on diet No. 5.

Follow-up examination in 1.5 months:

In USE: isolated stones, 1 and 2 mm in size.

According to laboratory examination, no pathology was detected.

Recommended: continue the therapy for up to 3 months.

After 3 months: in USE—signs of chronic cholecystitis, no concrements.

Conclusion: chronic cholecystitis in the remission phase.

2. Patient B., male, 45 years old.

On admission, complaints of anorexia, weakness, nausea, periodic vomiting, aching pain in the right hypochondrium after a large or fatty meal. In anamnesis: chronic alcoholism. Primary biliary cirrhosis. Had been treated irregularly.

Objectively: subnutrition. Dry skin, hot to the touch. Light yellow skin, icteric sclera. Above the lungs—pulmonary bandbox sound. Diminished breath sounds, diffused dry rales over the entire lung surface. Breathing rate: 20 a minute. Cardiac border expanded 1.0 cm to the left. Deadened sounds. Regular rhythm, second sound accent above the aorta. Soft abdomen, the right edge of the liver protrudes 2.0 cm from under the coastal arch, the edge is solid. Spleen not enlarged. Pasternatsky's syndrome was doubtful. Provisional diagnosis: primary biliary cirrhosis?

Examination:

Complete blood count: Hb 117 g/l; erythrocytes (Er) 3.5× 10/l; color index (CI) 0.9; leukocytes 4.0×10%; stab (S)—17%, leukocytes (L) 6%; segmental leukocytes (C) 36%; eosinophils (E) 5%; lymphocytes (L) 35%; monocytes (M) 1%; ESR 40 mm/h. Complete urinalysis: relative density 1012; no protein or glucose detected; leukocytes 0-2-3 in field of view; erythrocytes 0-2 in field of view; urine amilase 14.7 mgs/l.

Coprogram: muscle fibers without striation—a little; fatty acids—moderate amount; phytogenic fiber.

Blood biochemistry:

bilirubin and its fractions: total bilirubin (TB)—28.4 µmol/l (N—3.4-20.5 µmol/l); conjugated bilirubin (CB)—4.8 µmol/l (N—0.5-3.4 µmol/l), non-conjugated bilirubin (NCB)—15.0 µmol/l (N—2.56-10.3 µmol/l);

thymol test (TT)—16.1 units (N—4 units), ACT—90 units (N—60 units) GPT—74 units (N—50 units), alkaline phosphatase (ALP)—700 units (N—up to 295 units), sugar 6.6 mmol/l (N—44-6.6 mmol/l);

cholesterol and its fractions: total cholesterol (TC)—5.9 mmol/l (N—3.65-5.2 mmol/l), high-density lipids cholesterol (HDLC)—10.8 mmol/l (N—0.9-1.9 mmol/l), low-density lipids cholesterol (LDLC)—3.6 mmol/l (N—1.91-2.6 mmol/l), cholesterol atherogenic ratio (CAR) 3.9 c.u. (N—up to 3 c.u.), CCC 16.3 (N—up to 12); (norm up to 50); protein fractions: total protein 63 g/l (N 65-85 g/l); albumins 34 g/l (N—36-50 g/l);

antibodies: AMA in titer 1:45;

coagulogram: PTR 24 s—79%; thrombine clotting time 31 s; free heparin 11 s; fibrinogen 2.0 g/l; fibrinolytic activity>221 min.

Feces on dysbacteriosis: reduction of lactobacilli and bifidobacteria: lactobacilli (104), bifidobacteria (106).

Radiography of the liver and bile passages—the liver size increased by 2.5 cm due to the right lobe, distinct edges, indirect signs of biliar cirrhosis. Recommended: USE of the liver and gallbladder.

USE of the liver—signs of slight fatty infiltration of the liver and gallbladder cholesterosis. Pancreas not enlarged. Intra- and extrahepatic bile ducts not dilated.

No signs of portal hypertension detected.

No portal hypertension detected [sic].

Liver biopsy: Dilated portal tracts infiltrated by lymphocytes, plasma cells, macrophages and eosinocytes. Among the cells of portal tract infiltrates, lymphoid follicles are formed. Infiltrates are detected in walls of some intralobular bile ducts. Here and there, the integrity of the bile ducts' basic membrane is violated. Near the damaged bile ducts there are granulomas built of epithelioid and gigantic multinucleate cells.

Conclusion: biliary cirrhosis.

EKG—sinus rhythm, signs of moderate left ventricular hypertrophy. BP 150/85 Hg; heart rate 76 a minute.

Final diagnosis: lipid metabolism disorder, hypercholesterinemia. Primary biliary cirrhosis.

Treatment: the use of the claimed composition, wherein the active agents are a hepatoprotector—CDCA, and FOS in the ratio of 1:250 (unit dose of CDCA is 250 mg), orally 3 times a day at meal time for 1.5 months while on diet No. 5.

Follow-up examination in 1.5 months:

In USE: positive dynamics—reduction of fatty infiltration of the liver. In blood tests: reduction of hypercholesterinemia OX—4.6 mmol/l, HDLC—1.2 mmol/l, CCC 13.2; TB—21.5 µmol/l, AMA 1:30; total protein—72 g/l, albumins—34%, blood sugar 5.3 mmol/l, alkaline phisohatase—301 units, ACT—70 units, GPT—62 units, TT—8.1 units. Feces test on dysbacteriosis: lactobacilli $10^6$, bifidobacteria—$10^7$.

Recommended: continue the therapy for up to 3 months.

After 3 months—AMA 1:15, bifidobacteria $10^9$/g, lactobacilli $10^7$/g.

Conclusion: first degree primary biliary cirrhosis (significant positive dynamics).

3. Patient F., female, 50 years old.

On admission: there were complaints of apparent weakness, a feeling of weight and aching pain in the upper right abdomen area that appear for no apparent reason, anorexia, nausea, periodic vomiting, a feeling of bitterness in the mouth, stool softening, sometimes diarrhea, skin itch, changed color of the urine (lighter) and stool (lighter). From anamnesis: has had type 2 diabetes for 15 years, has been taking bukarban, a hypoglycemic agent. Has been under medical supervision by an endocrinologist and a district physician. Has been undergoing regular inpatient treatment at the endocrinology department, but without much effect. Associates the latest aggravation with virus infection (protracted course; complication: acute bronchitis, was taking antibacterial agents—cephalosporins).

Objectively: supernutrition—third degree obesity, body mass index (BMI) 34, pale skin, with traces of scratches on the abdomen and inner thighs. Icteric sclera. Abdomen greatly increased in size; soft, painful at Kehr's point. The liver protrudes 2.5 cm from under the coastal arch, the edge is solid. Spleen not enlarged. Diminished vesicular breathing in the lungs (because of fatty tissue). Breathing rate 22 a minute. Heart borders extended 1.0 cm to the right, 1.5 cm to the left. Deadened sounds, regular rhythm, soft systolic murmur over the apex of the heart. Heart rate was 76 a minute, BP 160/85 mm Hg. Pasternatsky's symptom was doubtful on both sides. Provisional diagnosis: fatty hepatosis (?), type 2 diabetes, third degree obesity.

Examination:
Complete blood count: Hb 121 g/l; erythrocytes (Er)—4.15×$10^{12}$/l; color index (CI)—0.89; leukocytes—3.8×10/l; stab (S) leukocytes (L)—7%; segmental leukocytes (S)—40%; eosinophils (E)—5%; lymphocytes (L) 45%; monocytes (M) 3%; ESR 39 mm/h. Blood glucose—6.8 mmol/l.
Complete urinalysis: relative density 1016; protein—traces; leukocytes 3-5 in field of view; erythrocytes 0 in field of view; urine amylase 16.2 mgc/l. Coprogram: muscle fibers without striation—a little; fatty acids—moderate amount; undigested phytogenic fiber—a lot; starch; isolated cells.
Feces on dysbacteriosis: Reduction of the number of bifidobacteria and lactobacilli, $10^5$/g and $10^6$/g (respectively) due to increased *Candida* fungi.
Blood biochemistry:
bilirubin and its fractions: total bilirubin (TB)—27.0 µmol/l (N 3.4-20.5 µmol/l); conjugated bilirubin (CB)—3.6 µmol/l (N—0.85-3.4 µmol/l, non-conjugated bilirubin (NCB)—11.2 µmol/l (N—2.56-10.3 µmol/l);
thymol test (TT)—8.0 units (N—4 units), ACT—69 units (N—60 units) GPT—76 units (N—50 units), thymol test (TT)—1.7 units (N—4 units), alkaline phosphatase (ALP)—346 units (N—up to 295 units), CCC 15.3; sugar 6.9 mmol/l, (N—4.4-6.6 mmol/l);
cholesterol and its fractions: total cholesterol (TC)—5.9 mmol/l (N—3.65-5.2 mmol/l), high-density lipids cholesterol (HDLC)—0.8 mmol/l (N—0.9-1.9 mmol/l), low-density lipids cholesterol (LDLC)—3.6 mmol/l (N—1.91-2.6 mmol/l), cholesterol atherogenic ratio (CAR) 3.8 c.u. (N—up to 3 c.u.), CCC 16.3 (N—up to 12);
triglycerides: 1.94 mmol/l (N—0.45-1.82 mmol/l)
protein fractions: total protein 67 g/l (N—65-85 g/l); albumins 38 g/l (N—36-50 g/l).
coagulogram: PTR 24 s—79%; thrombine clotting time 35 s; free heparin 12 s; fibrinogen 2.2 g/l; fibrinolytic activity>240 min.
Coprogram: dysbacteriosis due to reduction of lactobacilli and bifidobacteria—lactobacilli ($10^4$) (N>=$10^7$/g), bifidobacteria ($10^6$) (N>=$10^9$/g).
Radiography of the liver and bile passages:
uniform enlargement of the liver, no concrements.
Recommended: USE of the liver and bile passages.
USE of the liver—second degree hepatomegalia. Pancreas not enlarged.
Intra- and extrahepatic bile ducts not dilated. Signs of portal hypertension.
Esophagogastroduodenoscopy: esophageal veins dilatation в/3.
EKG—sinus rhythm, signs of moderate left ventricular hypertrophy, incomplete right bundle-branch block, BP 160/85 mm Hg;
Heart rate 74 a minute.
Final diagnosis: lipid metabolism disorder, triglyceridemia. Fatty hepatosis. Type 2 diabetes. third degree obesity.
Treatment: the use of the claimed composition, wherein the active agents are a hepatoprotector—essential phospholipids, and FOS in the ratio of 1:50 (the unit dose of essential phospholipids is 50 mg), orally 3 times a day at meal time for 1.5 months while on diet No. 5.

Follow-up examination in 1.5 months:
The patient notes a reduction of skin itch, increased activity; itch practically does not bother her, notes a 5 kg weight reduction. In USE: reduction of the liver size noted. Conclusion: fatty hepatosis, first degree hepatomegaly.
According to laboratory examination, reduction of triglycerides—1.82 mmol/l and total cholesterol—5.0 mmol/l, blood sugar has normalized—4.9 mmol/l, In feces analyses, significant increase of lactobacilli and bifidobacteria—$10^7$/g and $10^9$/g (respectively), is noted; no *Candida* fungi detected.
Recommended: continue the therapy for up to 3 months.
After 3 months, in USE—signs of moderate hepatomegaly. Blood tests—no peculiarities. Intestinal microflora has been restored: lactobacilli $10^7$/g, bifidobacteria 109/g.
Conclusion: fatty hepatosis, signs of moderate hepatomegaly. Type 2 diabetes; compensation; third degree obesity.

Example 4

Testing Acute Toxicity of the Compositions. The composition of UDCA and lactulose in the ratio of 1:2 (group 1), UDCA and FOS in the ratio of 1:50 (group 2), essential phospholipids (lecithin) and galactooligosaccharides in the ratio of 1:30 (group 3), ademethioninea and lactulose in the ratio of 1:50 (group 4) was administered orally to outbred white mice with a body mass of 15-20 g. The control group (group 6) was administered an equal amount of starch suspension. The animals were monitored for 4 days, and their general condition (appearance, mobility (activity), the regularity of food and water intake, the appearance and character of excrements) was recorded.

| Mixture (Group) | Maximum Amount of Administered Preparation (g) | Survival Rate (Alive/ Died) | Appearance | Diet | Motility | Excrement Appearance And Character |
|---|---|---|---|---|---|---|
| 1 | 2 | 6/0 | N | N | N | N |
| 2 | 2 | 6/0 | N | N | N | N |
| 3 | 2 | 6/0 | N | N | N | N |
| 4 | 2 | 6/0 | N | N | N | N |
| 5 | 2 | 6/0 | N | N | N | N |
| 6 | 2 | 6/0 | N | N | N | N |

Based on the results of the examination, there was no evidence of acute toxicity of each composition under the experimental conditions—all mixtures pertain to the class of low toxicity substances (LD50 values exceed 100 g/kg of body mass). Thus, the claimed pharmaceutical composition that includes as active agents a hepatoprotector and a prebiotic selected from a non-digestible in the intestine oligosaccharides can be recommended for use under clinical conditions for the treatment and prevention of liver diseases selected from the following group: cholelithiasis, fatty hepatosis and nonalcoholic steatohepatitis, primary biliary cirrhosis, gall bladder cholesterosis, and drug-induced and toxic liver injury.

What is claimed is:
1. A pharmaceutical composition for a treatment and prevention of recurrences of liver diseases in human caused by a disturbance of lipid-cholesterol metabolism, wherein the liver diseases are selected from a group including cholelithiasis with mainly cholesterol stones, alcoholic and nonalcoholic steatohepatitis, primary biliar cirrhosis, gall bladder cholesterosis, and drug-induced and toxic liver injury, the composition, comprising:

a mixture of a hepatoprotector and a prebiotic combined together in effective doses in a ratio of 1:2 to 1:250 by mass of pure substances; the mixture being taken by a person orally, the doses leading to a restoration of liver functions in a period of about 1.5 months and prevention of exacerbations of liver diseases; wherein the hepatoprotector comprises ursodeoxycholic acid (UDCA) and the prebiotic comprises lactulose.

2. The pharmaceutical composition according to claim 1, wherein the hepatoprotector further comprises amino acids.

3. The pharmaceutical composition according to claim 1, wherein the hepatoprotector further comprises active components of milk thistle plant extracts.

4. The pharmaceutical composition according to claim 1, wherein the hepatoprotector further comprises essential phospholipids.

5. The pharmaceutical composition according to claim 1, wherein the hepatoprotector further comprises other bile acids or bile acid salts.

6. The pharmaceutical composition according to claim 5, wherein the bile acids or bile acid salts are selected from the group consisting of chenodesoxycholic acid (CDCA), desoxycholic acid (DCA), lithochloic acid (LCA), taurodesoxycholic acid (TDCA), hyodeoxycholic acid (HDCA), taurocholic acid (TCA), glycochloic acid (GCA), and combinations thereof.

7. The pharmaceutical composition according to claim 1, wherein the prebiotic further comprises fructooligosaccharides.

8. The pharmaceutical composition according to claim 1, wherein the prebiotic further comprises maltooligosaccharides.

9. The pharmaceutical composition according to claim 1, wherein the prebiotic further comprises galactooligosaccharides.

10. The pharmaceutical composition according to claim 1, wherein the prebiotic further comprises xylooligosaccharides.

11. The pharmaceutical composition according to claim 1, wherein the prebiotic is lactulose in a ratio of 1:2 by mass of pure substances.

12. The pharmaceutical composition according to claim 1, wherein the hepatoprotector further comprises essential phospholipids selected from a group consisting of phosphatidylcholin, phosphatidylethanolamine and phosphatidylinositol, in a ratio of the essential phospholipids and the prebiotic is from 1:0.1 to 1:100 by mass of pure substances.

13. The pharmaceutical composition according to claim 1, wherein the hepatoprotector further comprises active components of milk thistle plant extracts selected from silimarin or silibin, and a ratio of the active components of milk thistle plant extracts and the prebiotic is from 1:0.1 to 1:100 by mass of pure substances.

14. The pharmaceutical composition according to claim 1 made in the form of tablets, granules, globules, powders or capsules, suspensions, pastes, syrups, emulsion, or gels intended for oral administration 2-3 times a day.

15. The pharmaceutical composition according to claim 1, wherein the hepatoprotector and the prebiotic are taken in effective doses in a ration of 1:2 to 1:50 by mass of pure substances.

* * * * *